United States Patent [19]

Sakamoto et al.

[11] Patent Number: 4,668,472

[45] Date of Patent: May 26, 1987

[54] SLIDE FOR CHEMICAL ANALYSIS

[75] Inventors: Norio Sakamoto, Hino; Toshiyuki Ikariya, Hachioji; Kiyohiko Takahashi, Hino; Masao Nakamura, Machida; Akira Yanagisawa, Akigawa, all of Japan

[73] Assignee: Konishiroku Photo Industry Co., Ltd., Tokyo, Japan

[21] Appl. No.: 672,098

[22] Filed: Nov. 15, 1984

[30] Foreign Application Priority Data

Nov. 24, 1983 [JP] Japan ................. 58-221126

[51] Int. Cl.$^4$ ............... G01N 21/78; G01N 33/52
[52] U.S. Cl. .................... 422/56; 40/158 B; 206/305; 206/455; 422/58; 422/104
[58] Field of Search ............ 422/58, 61, 56, 66, 422/102, 104; 206/305, 455, 456; 356/244, 246; 40/158 R, 158 B

[56] References Cited

U.S. PATENT DOCUMENTS

| | | | |
|---|---|---|---|
| 3,620,678 | 11/1971 | Guigan et al. | 422/66 |
| 3,666,421 | 5/1972 | Price | 422/58 X |
| 3,689,224 | 9/1972 | Agnew et al. | 422/61 |
| 4,181,500 | 1/1980 | Cowsar et al. | 422/58 X |
| 4,230,757 | 10/1980 | Toner | 422/56 X |
| 4,275,031 | 6/1981 | Fischer et al. | 422/58 |
| 4,328,184 | 5/1982 | Kondo | 422/58 |
| 4,387,990 | 6/1983 | Yazawa et al. | 422/102 X |

Primary Examiner—Arnold Turk
Attorney, Agent, or Firm—Frishauf, Holtz, Goodman & Woodward

[57] ABSTRACT

A process for the continuous preparation of slides to be chemically analyzed comprises forming regularly a plurality of hollows on an advancing web material; putting a piece of film to be chemically analyzed in each of the hollows; sticking a long covering member having a plurality of apertures corresponding in their positions to the hollows on the web material onto the surface of the web material so that the apertures and the hollows on the web material are in registration; and cutting the circumference outside of each of the hollows. Also disclosed is a slide to be chemically analyzed which comprises a web material having a hollow in the central region thereof in which a film to be chemically analyzed is put, a covering member having an aperture on the surface thereof stuck to the web material; and downwardly extending flanges on a circumferential portion of the slide having heights substantially equal to that of the hollow to stabilize positioning of the slide.

10 Claims, 8 Drawing Figures

SLIDE FOR CHEMICAL ANALYSIS

BACKGROUND OF THE INVENTION

This invention relates to a continuous preparation process of slides with which the composition of a liquid can chemically be analyzed and measured the same and, more particularly, to continuous preparation process of such slides of which every film frame for chemically analyzing the compositions of liquid samples respectively through the measurement of the optical density thereof is automatically set in the respective slide mounts.

Various dry multilayer-integration type films for chemically analytic use are known, with which quantitative analyses of the contents of specific components of liquid samples such as those of blood, serum, urine and the like can easily and rapidly be performed. Such films are disclosed in U.S. Pat. Nos. 3,992,158, 3,983,005, 4,042,335, 4,066,403 and the like.

Such films for chemically analytic use comprise, as shown in FIG. 3, a transparent support 10a laminated thereon with reagent layer 10b and porous spreading layer 10c in order so as to be constructed in a body or to remove the support 10a.

When a liquid sample is dropped on the spreading layer of film for chemically analytic use, the sample is spread uniformly over the surface of the spreading layer and at the same time it permeates the reagent layer to react it with the reagent, so that a coloration or discoloration occurs. The value of this coloration is measured from either side of the spreading layer or the support by the use of an optical densitometer. The contents of the specific components of the liquid sample is figured out from the value measured. The film for chemically analytic use is supplied in the form of being set in a slide mount similar to those for known transparent positive photographic films. For example, such slide mount is constructed, as typically described in Japanese Patent Publication Open to Public Inspection No. 63452/1982, so that a film for chemically analytic use may be sandwiched between the first mount and the second mount each having an opening smaller than the surface area of the film for chemically analytic use. The well-known slide mount described above has a disadvantage that the cost will be too high to serve as a test piece, because it requires an intermediate member in addition to the first and second mounts and the assembling process of the mount will be complicated and consequently a large-scaled installation must be required.

OBJECTS OF THE INVENTION

It is an object of the invention to provide a continuous preparation process of slides for chemically analytic use, in which a number of slides for chemicaly analytic use can readily be prepared.

Another object of the invention is to provide a continuous preparation process of slides for chemically analytic use, in which a web material is cut out to form a number of slide mounts each comprising a thermoplastic resin molding to which a frame for fixing a film for chemically analytic use as a slide mount for optical density measurement is provided.

A further object of the invention is to provide a slide for chemically analytic use having a novel shape.

SUMMARY OF THE INVENTION

This invention relates to a continuous preparation process of slides for chemically analytic use, in which a plurality of hollows are formed on and regularly arranged to a web material being moved and films for chemically analytic use are put in the hollows respectively, and further the web material is cross cut from the area where the films are not put in so as to make a plurality of slides for chemically analytic use; and more particularly to a continuous preparation process of a plurality of slides for chemically analytic use, in which a number of hollows are formed on and arranged regularly to a web material being moved and films for chemically analytic use are put in the hollows respectively and then the surface of the web material is continuously laminated thereon with a long covering member having the apertures corresponding to the hollows so that the apertures and the hollows can be corresponded respectively, and further the lamination is cut out in the circumference of the hollows to make a plurality of slides for chemically analytic use. This invention also relates to a novel slide for chemically analytic use comprising a web material having a hollow in which a film for chemically analytic use is put and a covering member having an aperture positioned over the hollow, and further relates to a novel slide for chemically analytic use having flange members on the rear side of a web material.

The web materials of the slides for chemically analytic use of the invention comprise a thin plate made of a synthetic resin, a natural fiber, a synthetic fiber, a metal foil or the like, and the suitable ones are synthetic resin sheets including, for example, those of vinyl chloride, polystyrene, polyethylene terehthalate or the like which are used for the supports of photographic films.

The web materials are provided regularly with hollows (i.e., processed to make cave in by a commonly known bending machine (i.e., a drawing machine) or the like.

To the hollows of a moved web material are put in with films for chemically analytic use each comprising a separately prepared spreading layer and reagent layer disclosed in U.S. Pat. No. 3,992,158, and on the surface thereof is laminated with a covering member comprising a thin layer in the quality equivalent to that of the web material. The covering member includes apertures so as to correspond to the hollows of the sheet shaped support material, respectively. When laminating the covering member, every aperture must be positioned respectively so as to meet the surfaces of the films for chemically analytic use put in the hollows of a web material. This lamination is then moved to a cutter to be cut out from the portions where the web material is laminated with the covering member, so as to prepare slides for chemically analytic use continuously.

To the rear side of the web material is provided with flanges whose height is equal to the height of the hollows of the slides, so that the slides can stably be placed when storing or using.

Figure 1:
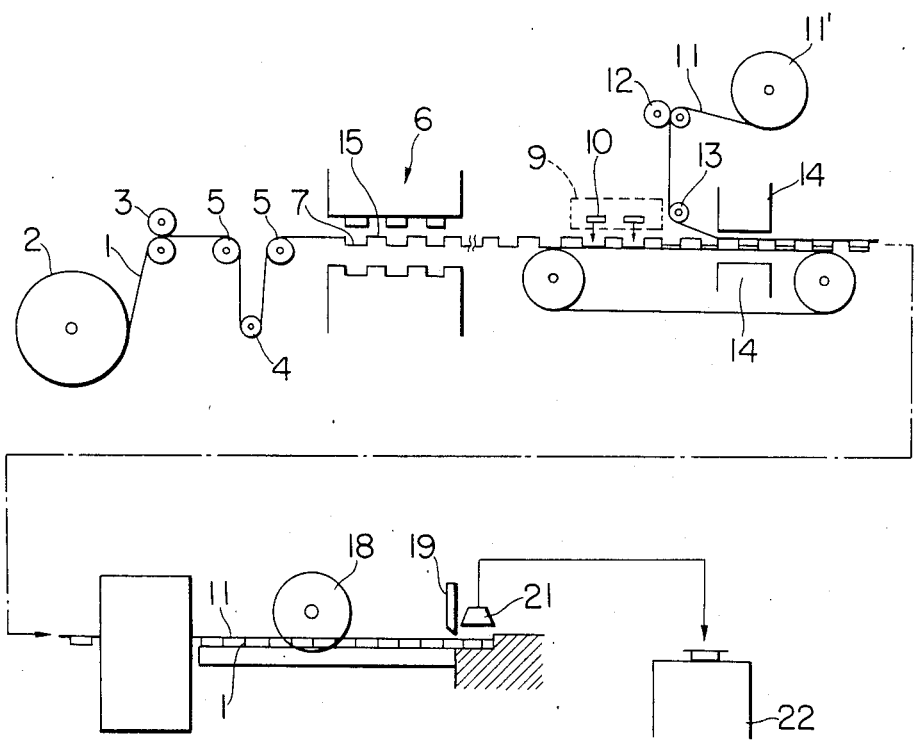
FIG. 1 is a schematic diagram showing a continuous preparation process of slides to be chemically analyzed of the present invention.

Referring to the example shown in attached drawings, the present invention will be explained as follows.

The numeral 1 represents a web material in the shape of a continuous sheet and the web material 1 is drawn out through a take-up roller 3, a tension roller 4 and guide rollers 5 and then advances horizontally on a work table which is not illustrated.

Figure 2:
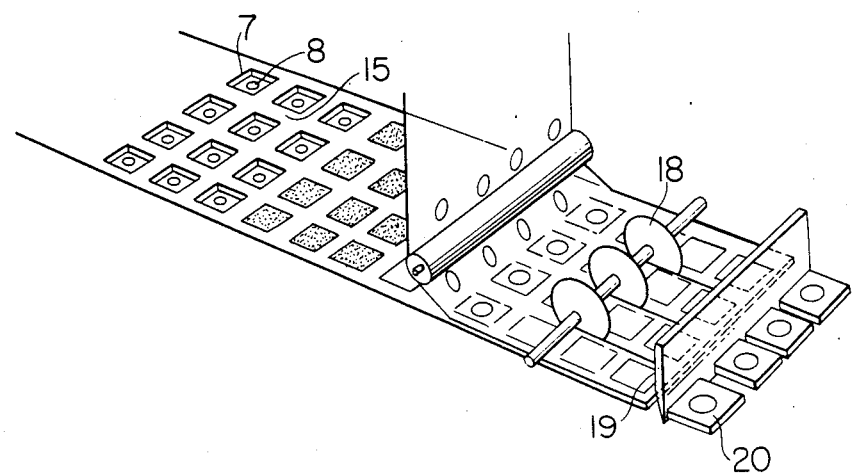
FIG. 2 is a perspective view showing the primary part of the preparation steps.

The numeral 6 is a drawing device which makes hollows downward on the web material drawn out as described above and in this illustration, the drawing press is shown as the drawing device 6 but it is naturally possible to use a vacuum forming machine or a pneumatic forming machine. This drawing device 6 forms hollows 7 regularly. When the web material 1 is opaque, the aperture 8 (see FIG. 4) for photometry is made at the center portion of the bottom of the hollow and this aperture can be made by the drawing device 6 together with the forming of the hollow 7 or it may be made by the exclusive hole-boring machine (not shown) located at preceding or following step of the drawing device 6. FIG. 2 shows an example of the arrangement of hollows but an arrangement is not limited to the example of FIG. 2 if the hollows are arranged regularly.

The numeral 9 is a loader that puts the film to be chemically analyzed 10 comprising a transparent support, a reagent layer formed on the transparent support and a spreading layer laminated on the spreading layer, in the hollow 7 formed as stated above. The loader 9 whose details are not illustrated, has only to be the one which receives from the supplier (not shown) the films to be chemically analyzed in a fixed size, arranges them in line, transports them to the point right above the hollow 7 where the means like the vacuum sucker device picks them up and the sucker end thereof is lowered by the driving means like a crank arm so that the film to be chemically analyzed 10 can be loaded in aforesaid hollow 7.

Figure 3:
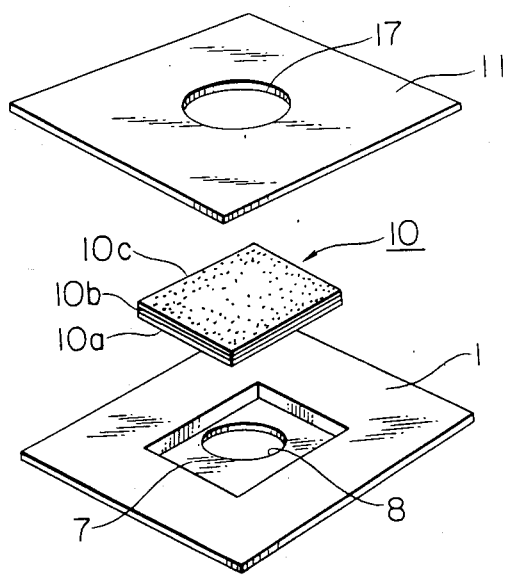
FIG. 3 is an exploded perspective view of a slide to be chemically analyzed prepared through the preparation process of the present invention and FIG. 4 through FIG. 8 are perspective views showing the center sections of other examples.
Figure 4:
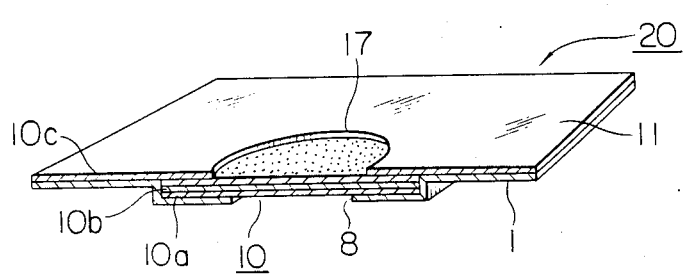

The film to be chemically analyzed 10 consists, as shown in FIG. 3 and FIG. 4, of a transparent support 10a, a reagent layer 10b formed on the upper side of the transparent support and a spreading layer 10c laminated on the reagent layer. The purpose of the spreading layer 10c is to cause liquid sample dripped thereon to spread in the direction of a plane and to react on the reagent layer 10b.

The numeral 11 is a long covering member which is in a form of a roller wound round the reel 11' and is drawn out through the take-up roller 12 and then is supplied through the guide roller 13 on the upper side of the web material 1 after the film to be chemically analyzed 10 is put in, aforesaid hollow 7 so that the covering member is stuck to the adhesion portion 15 between hollows 7.7... by the application device 14. This adhesion means generally employs an ultrasonic adhesion but other adhesion means is also acceptable if it secures a firm adhesion which is not easily peeled off.

Further, the apertures 17 for dripping the sample are made in advance on this long covering member 11 at the locations each of which corresponds to the central portion of the hollow 7. The location of each aperture may precisely correspond to that of the hollow 7 formed by aforesaid drawing device 6 when the timing is adjusted with the advancing speed of the hollow 7.

The numeral 18 is a slitter that slits longitudinally the area corresponding to the center of the adhesion portion 15 of aforesaid web material 1 after the long covering member is supplied and stuck on the top surface of the web material 1, and the slitter 18 employs a rotary knife which meets the requirements for the slitter. The numeral 19 is a cross-cutter that cuts laterally web material 1 and covering member 11 after they are slitted by the slitter 18 and the products 20 shown in FIG. 3 are obtained continuously through the cutting by the cross-cutter 19 shown in FIG. 2. The cutting method may be the one other than that shown in FIG. 2 if the cutting can correspond to the hollows which are regularly arranged. As can be seen in FIG. 3, the hollow 7 protrudes downwardly from the bottom of a substantially central portion of the web material.

Incidentally, 21 in the figure is a pick-up device that picks the products 20 up from the line and 22 is a storage rest therefor.

It is desirable that aforesaid web material 1 will be prepared through the plastic molding from the viewpoints of productivity, operability and cost, and the hollow 7 in which aforesaid film to be chemically analyzed 10 is put is provided at the central area thereof. Any means among pneumatic forming, vacuum forming and press forming for the formation of the hollow 7 gives the same result. Aforesaid web material 1 may be made from transparent plastic material in some cases or from opaque plastic material in other cases. In the former case, it is not necessary to provide the hole for photometry on the bottom of the hollow 7 because the film to be chemically analyzed 10 loaded in the hollow 7 can be seen through but in the latter case, it is required that the hole 8 for photometry is provided on the bottom of the hollow 7 as shown in the figure. The diameter of the hole 8 is to be decided in accordance with the illumination area of the light for photometry.

FIG. 3 through FIG. 8 show the film to be chemically analyzed 10 laminated, in the order from the bottom, with a transparent support 10a, a reagent layer 10b and a spreading layer 10c. Above order of the lamination may be reversed and hole 8 may be used for the dripping of liquid sample and hole 17 may be used as a through hole for photometry. In this case, it is possible to place the slide with its covering member 11 located at the bottom, thus the slide may stably be placed, which is advantageous.

Aforesaid covering member 11 is to hold the film to be chemically analyzed 10 loaded in the hollow 7 of aforesaid web material 1 and it is stuck on the top surface of the web material 1 by means of a proper means (e.g. adhesion by an adhesive agent, ultrasonic deposition or mechanical binding etc.). In the central area of the covering member 11, there is provided a hole 17 through which the liquid sample is dripped. The diameter of the hole 17 for the dripping of liquid sample is to be decided considering the easiness of dripping and it is naturally smaller than the size of aforesaid film to be chemically analyzed.

Figure 5:
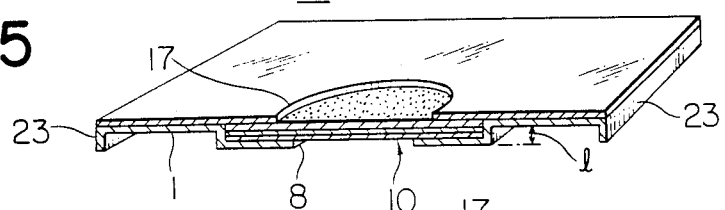
Figure 6:
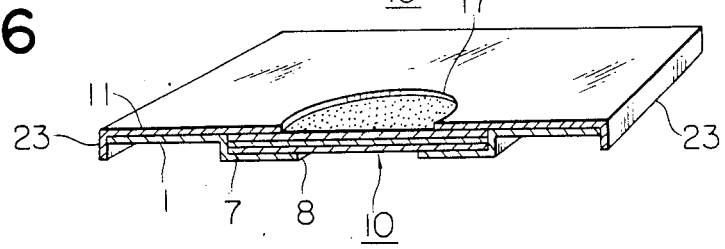
Figure 7:
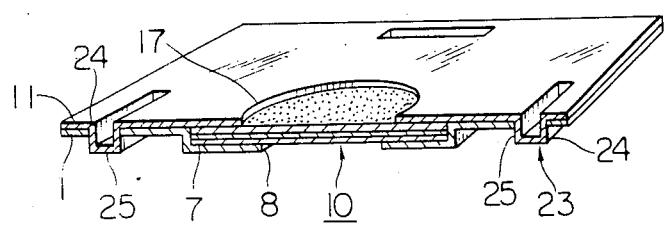
Figure 8:
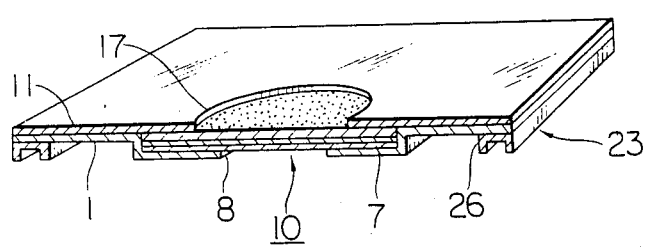

The numeral 23 is a flange member provided at a circumferential portion on the lower side of aforesaid web material 1 and it has a height substantially the same as the protruded value of aforesaid hollow 7. The purpose of the flange member 23 is to secure the easiness of keeping horizontality of aforesaid web material 1 when it is placed on the measuring board which is not illustrated or it is stored in a magazine, and typical examples thereof are shown in FIG. 5 through FIG. 8. As can be seen in these Figures, there are downwardly extending flanges on a circumferential portion of the web material or the covering member. The flanges are located outside of and spaced a substantial distance from the hollow and have a thickness in a transverse direction of the slide which is substantially less than the transverse dimension of the slide. In FIG. 5, the circumference of aforesaid web material 1 is bent down to be used as the flange member 23 and this type has a merit that the flange member 23 can be formed together with the formation of the hollow 7. In FIG. 6, the circumference of aforesaid covering member 11 is bent down and is used as the flange member 23. In this case, the flange member 23 functions as a connecting means for the web material 1 and the covering member 11. In FIG. 7, the apertures 24 are made on the periphery of aforesaid web material 1 and protrusions 25 are provided on the lower surface of the periphery of the covering member 11 so that the protrusions 25 passing through the apertures 24 are used as flange members 23. In this case, the flange members 23 are on two pairs of opposing sides of the hollow and function also as a connecting means for the web material and the covering member 11. FIG. 8 shows an example in which the form members 26 such as groove-forms or I-forms are attached on the periphery of aforesaid web material 1 and are used as flange members 23.

Since the slides to be chemically analyzed of the present invention can be prepared continuously by forming the hollows on the web material while it is being transported and by putting the films to be chemically analyzed in the hollows and cutting them one by one, they can be prepared in a simpler way and in a shorter time compared with the method wherein a plurality of slide frames are assembled and formed to be the slide to be chemically analyzed, thus the simplification of manufacturing facilities and the reduction in cost can be expected. The novel slide to be chemically analyzed thus manufactured is of a construction of two sheets of the web material whose central area on its upper side is drawn into the hollow and of the covering member that holds the film to be chemically analyzed loaded in the hollow of the web material and therefore the number of its structure items is small and it has an excellent effect that the forming and assembling steps for the slide to be chemically analyzed are simplified and the slide to be chemically analyzed can be offered at a low price.

When the slide to be chemically analyzed of the present invention is provided, at its circumference on its lower side, with flange members whose height compares with the protrusion value of the hollow, the flange members are effective for keeping horizontality of the slides to be chemically analyzed placed on the measuring board or stored in the container such as a magazine, despite the hollow that is small compared with the area of the slide.

What is claimed is:

1. A slide to be chemically analyzed, comprising:
   a web material having a hollow substantially in a central region thereof, said hollow protruding downwardly from the bottom of a substantially central portion of said web material, said web material having an upper surface surrounding said hollow;
   a film received in said hollow and which is to be chemically analyzed;
   a covering member stuck to said upper surface of said web material for covering at least a portion of said hollow to retain said film in said hollow, said covering member having an opening therein in communication with said hollow, said opening being smaller than said film so as to prevent said film from coming out of said hollow; and
   downwardly extending flanges on a circumferential portion of said web material or covering member and located outside of and spaced a substantial distance from said hollow, said flanges each having a height substantially equal to that of said hollow to stabilize positioning of said slide in use, said flanges having a thickness in a transverse direction of said slide which is substantially less than the transverse dimension of said slide.

2. A slide as claimed in claim 1, wherein said flanges comprise bent-over peripheral portions of said web material.

3. A slide as claimed in claim 1, wherein said flanges comprise flange members secured to the underside of circumferential portions of said web material.

4. A slide as claimed in claim 1, wherein said web material comprises openings at circumferential portions thereof, and said covering material extends through said openings in the direction of said hollow to form said flanges.

5. A slide as claimed in claim 1, wherein said covering member is adhesively secured to an upper surface of said web material.

6. A slide as claimed in claim 1, wherein said flanges are integrally formed on said slide from at least one of said web material and covering member.

7. A slide as claimed in claim 1, wherein said flanges comprise bent-over peripheral portions of said covering member.

8. The slide of claim 7, wherein said bent-over portions of said covering member extend around peripheral portions of said web material.

9. A slide as claimed in claim 1 wherein said flanges are arranged at least on two opposite sides of said hollow.

10. A slide as claimed in claim 9, wherein said flanges are arranged at least on two pairs of opposing sides of said hollow.

* * * * *